United States Patent [19]

Shibukawa et al.

[11] 4,418,061

[45] Nov. 29, 1983

[54] SECALONIC ACID DERIVATIVES AND METHOD FOR PREPARING THEREOF

[75] Inventors: Mitsuru Shibukawa, Yokohama; Chisei Shibuya, Fuji; Kunihiko Ishii, Numazu, all of Japan

[73] Assignee: Asahi Kasei Kogyo Kabushiki Kaisha, Japan

[21] Appl. No.: 366,333

[22] Filed: Apr. 7, 1982

[30] Foreign Application Priority Data

Apr. 16, 1981 [JP] Japan .................................. 56-56219
Apr. 25, 1981 [JP] Japan .................................. 56-61916

[51] Int. Cl.³ .................... C07D 405/14; A61K 31/40
[52] U.S. Cl. .................................... 424/245; 424/274; 548/454; 548/525; 548/402; 549/212; 549/415
[58] Field of Search ................ 548/454, 525, 402; 424/274, 245

[56] References Cited

U.S. PATENT DOCUMENTS 3,925,415 12/1975 Ishida et al. .................. 424/278

FOREIGN PATENT DOCUMENTS 57-171989 10/1982 Japan .

OTHER PUBLICATIONS

*The Merck Index*, 9th ed., (1976), p. 1090, #8170.
Howard et al., J. Chem. Soc. Comm., (1973), p. 464.
Howard et al., J. Chem. Soc. Perkin I, (1973), p. 2440.
Anderson et al., J. Org. Chem., 42, (1977), p. 352.

*Primary Examiner*—Mark L. Berch
*Assistant Examiner*—William A. Teoli, Jr.

*Attorney, Agent, or Firm*—Finnegan, Henderson, Farabow, Garrett & Dunner

[57] ABSTRACT

A secalonic acid derivative of the formula (I);

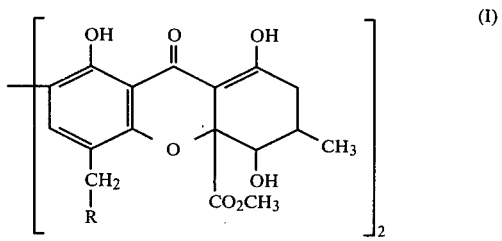

wherein R is

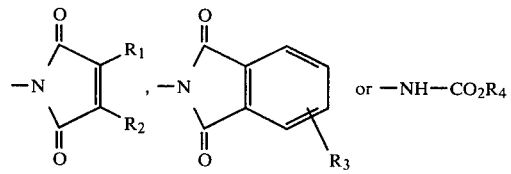

wherein $R_1$ and $R_2$ each independently is a hydrogen atom or a $C_{1-4}$ alkyl group; $R_3$ is a hydrogen atom, a $C_{1-4}$ alkyl group, an aryl group, a $C_{1-5}$ alkoxy group, a halogen atom, a cyano group, a carboxyl group, a sulfonic acid group, a carboxylic acid amide group or a sulfonic acid amide group; and $R_4$ is a saturated or unsaturated $C_{1-22}$ alkyl group, an aryl group or an aryl alkyl group, and may have a substituent;

and the pharmaceutically acceptable salts thereof.

7 Claims, No Drawings

SECALONIC ACID DERIVATIVES AND METHOD FOR PREPARING THEREOF

BACKGROUND OF THE INVENTION

1. Field of the Invention

This invention relates to novel secalonic acid derivatives and methods for the preparation thereof.

2. Description of the Prior Art

Seven stereoisomers of secalonic acid such as secalonic acids A, B, C, D, E, F and G have been isolated from fungi or Lichenes and reported by the following literature.

(1) Isolation of secalonic acids A, B and C from *Claviceps pururea* (B. Frank and E. M. Gottshalk, Angew. Chem. Internat. Edn., 1964, 3, 441; B. Frank, E. M. Gottshalk, U. Ohnsorge and F. Hüper, Chem. Ber., 1966, 99, 3842; D. J. Abehart, Y. S. Chen, P. de Mayo and J. B. Stothers, Tetrahedron, 1965, 21, 1417).

(2) Isolation of secalonic acids A and B from *Penicillium islandicum* (J. W. Apsimon, J. A. Corran, N. G. Greasey, W. Marlow, W. B. Whalley and K. Y. Sim, J. Chem. Soc., 1965, 4144).

(3) Isolation of secalonic acid A from *Parmelia entotheiochroa* (I. Yoshioka, T. Nakanishi, S. Izumi and I. Kitagawa, Chem. Pharm. Bull., 1968, 16, 2090).

(4) Isolation of secalonic acid D from *Penicillium oxalicum* (P. W. Steyn Tetrahedron, 1970, 26, 51).

(5) Isolation of secalonic acid A from *Aspergillus ochraceus* (M. Yamazaki, Y. Maebayashi and K. Miyaki, Chem. Pharm. Bull., 1971, 19, 199).

(6) Isolation of secalonic acid C from *Cetraria ornata* (I. Yoshioka, H. Yamauchi, K. Murata and I. Kitagawa, Chem. Pharm. Bull., 1972, 20, 1082).

(7) Isolation of secalonic acid A, E and G from *Pyrenochaeta terrestris* (C. C. Howard, R. A. W. Johnstone and I. D. Entwistle, J. Chem. Soc. Comm., 1973, 464; C. C. Howard and R. A. W. Johnstone, J. Chem. Soc. Perkin I, 1973, 2440; I. Kurobane, L. C. Vining and A. G. McInnes, Tetrahedron Letters, in press).

(8) Isolation of secalonic acids D and F from *Aspergillus aculeatus* (R. Anderson, G. Büchi, B. Kobbe and A. L. Demain, J. Org. Chem. 1977, 42, 352).

These secalonic acids are effective for an ascites carcinoma of mice and rats, however, they have such a drawback that they show a strong toxicity.

SUMMARY OF THE INVENTION

An object of this invention is to provide novel secalonic acid derivatives.

Another object of this invention is to provide a method for preparing novel secalonic acid derivatives.

A further object of this invention is to provide a novel antitumor agent.

Accordingly, the present invention in one embodiment provides secalonic acid derivatives having the formula (I),

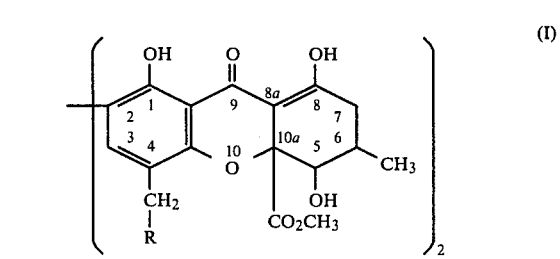

wherein R is

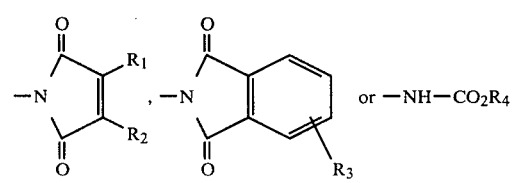

wherein
- $R_1$ and $R_2$ each independently is a hydrogen atom or a $C_{1-4}$ alkyl group;
- $R_3$ is a hydrogen atom, a $C_{1-4}$ alkyl group, an aryl group, a $C_{1-5}$ alkoxy group, a halogen atom, a cyano group, a carboxyl group, a sulfonic acid group, a carboxylic acid amide group or a sulfonic acid amide group; and
- $R_4$ is a saturated or unsaturated $C_{1-22}$ alkyl group, an aryl group or an aryl alkyl group, and may have a substituent;

and the pharmaceutically acceptable salts thereof.

DESCRIPTION OF PREFERRED EMBODIMENTS

The secalonic acid derivatives having the formula (I) of this invention are the compounds derived from the secalonic acid A, B, C, D, E, F or G of the formula (II),

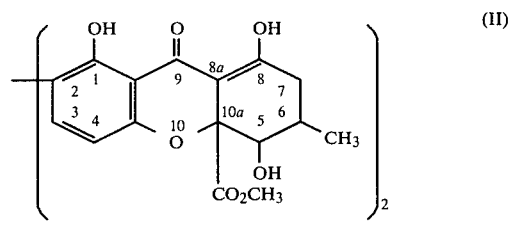

by substituting both the 4- and 4'-positioned hydrogen atom of the secalonic acid with a methylenemaleimide group, a methylenephthalimide group, or a methylenecarbamate group which is represented by

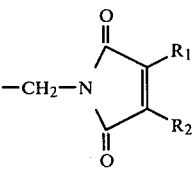

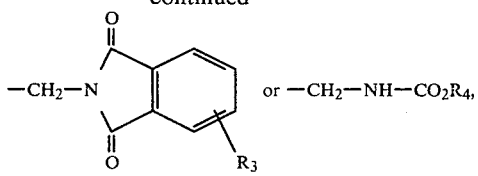

respectively. Preferred secalonic acids include secalonic acid A, D, E, F and G.

Exemplary $R_1$ and $R_2$ include a hydrogen atom and a $C_{1-4}$ alkyl group such as methyl, ethyl, n-propyl, sec-butyl and t-butyl group. Preferred $R_1$ and $R_2$ include a hydrogen atom and a methyl group. Exemplary maleimide group includes maleimide, α-methylmaleimide, α-ethylmaleimide, α-n-propylmaleimide, α-t-butylmaleimide, α,β-dimethylmaleimide, α,β-diethylmaleimide and α,β-di-sec-butylmaleimide. Preferred maleimide groups include maleimide, α-methylmaleimide and α,β-dimethylmaleimide.

Exemplary $R_3$ includes a hydrogen atom; a $C_{1-4}$ alkyl group such as methyl, ethyl, n-propyl and t-butyl group; an aryl group such as phenyl and tolyl group; a $C_{1-5}$ alkoxy group such as methoxy, ethoxy, propoxy and butoxy group; a halogen atom such as chlorine and bromine atom; a cyano group; a carboxyl group; a sulfonic acid group; a carboxylic acid amide group such as methylaminocarbonyl and n-propylaminocarbonyl group; and a sulfonic acid amide group such as aminosulfonyl and dimethylaminosulfonyl group. Preferred $R_3$ includes a hydrogen atom, a methyl group, a methoxy group and a chlorine atom. Exemplary phthalimide groups include phthalimide, 3-methylphthalimide, 3,4-dimethylphthalimide, 3-t-butylphthalimide, 2- or 3-phenylphthalimide, 2- or 3-methoxyphthalimide, 2- or 3-chlorophthalimide, 2- or 3-cyanophthalimide, 2- or 3-monocarboxyphthalimide, 2,3-dicarboxyphthalimide, 2- or 3-sulfophthalimide, 2- or 3-di-n-propylaminocarbonylphthalimide, 2- or 3-dimethylaminocarbonylphthalimide, 2- or 3-aminosulfonylphthalimide and 2- or 3-dimethylaminosulfonylphthalimide. Preferred phthalimide groups include phthalimide, 3-methylphthalimide, 3-methoxyphthalimide and 3-chlorophthalimide.

Exemplary $R_4$ includes a saturated $C_{1-22}$ alkyl group such as methyl, ethyl, n-propyl, iso-propyl, n-butyl, sec-butyl, t-butyl, n-pentyl, iso-pentyl, n-hexyl, cyclohexyl, n-nonyl, n-tridecyl, n-hexadecyl, n-octadecyl, n-eicosyl and n-docosyl group; an unsaturated alkyl group such as vinyl and allyl group; a substituted alkyl group such as 2-ethoxyethyl, 2,2,2-trichloroethyl, 2,2-dichloroethyl, 2-chloroethyl, 2-fluoroethyl, 2(2-methoxyethyloxy)ethyl and 2-nitroethyl group; an aryl group such as phenyl and nitrophenyl group; and an aryl alkyl group such as benzyl and nitrobenzyl group. Preferred $R_4$ includes a saturated $C_{1-22}$ alkyl group; a vinyl group; an allyl group; a substituted ethyl group with an ethoxy group, a nitro group or 1-3 chlorine atoms; a phenyl group; a nitrophenyl group; and a benzyl group.

The secalonic acid derivatives of the formula (I) can be converted into the salts of a monovalent metal such as sodium, potassium and lithium; the salts of a divalent metal such as calcium, iron (II), copper (II) and magnesium; the salts of a trivalent metal such as iron (III) and aluminum; the salts of an ammonium; and the salts of a nitrogen-containing organic base such as triethylamine, tributylamine, ethanolamine, triethanolamine, dibenzylamine, N,N-dibenzylethylenediamine, N-benzyl-β-phenethylamine, N-methylmorpholine, procaine, ephenamine, dibucaine, lidocaine and L-arginine.

Preferred salts of the secalonic acid derivatives of this invention include the metal salts such as sodium, potassium, magnesium, iron (III) and aluminum; and the salts of a nitrogen-containing organic base such as triethylamine, ethanolamine, triethanolamine, dibenzylamine, N,N-dibenzylethylenediamine, procaine, dibucaine and lidocaine. The sodium or aluminum salts of the secalonic acid derivatives are more preferred.

The secalonic acid derivatives of the formula (I) of this invention can be prepared by reacting the secalonic acid of the formula (II) with a N-methylol derivative of the formula (III) or a biscarbamate of the formula (IV):

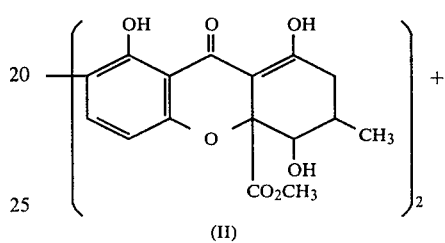

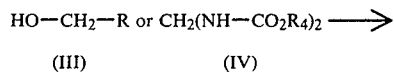

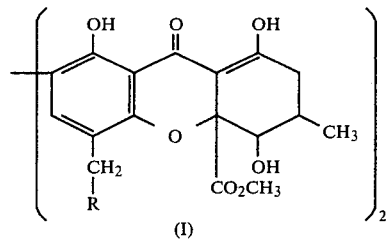

wherein R and $R_4$ are the same as defined in the formula (I).

Dehydrating agents or catalysts which can be employed in the reaction between the secalonic acid (II) and the N-methylol derivative (III) of the biscarbamate (IV) include inorganic acids such as concentrated sulfuric acid, fuming sulfuric acid, phosphoric acid, polyphosphoric acid and hydrogen fluoride; organic acids such as methanesulfonic acid, ethanesulfonic acid, ethanolsulfonic acid, trifluoromethanesulfonic acid, trifluoroacetic acid, trichloroacetic acid, acetic acid and formic acid; zinc chloride; aluminum chloride; phosphorus oxychloride; phosphorus pentoxide; boron trifluoride and boron trifluoride etherate. When the inorganic acid of the organic acid is employed in the reaction, the acid can act as a solvent besides the dehydrating agent and the catalyst.

The solvents inert to the reaction between the secalonic acid (II) and the N-methylol derivative (III) or the biscarbamate (IV) can be used in the reaction, if necessary. Exemplary solvents which can be employed include alcohols such as methyl alcohol and ethyl alcohol; aromatic hydrocarbons such as monochlorobenzene, dichlorobenzene, trichlorobenzene and nitrobenzene; hydrocarbons such as dichloromethane, dibromomethane, chloroform, 1,2-dichloroethane, tetrachloromethane and n-pentane; nitrogen-containing compounds such as pyridine, picoline, N,N-dimethylformamide and N,N-dimethylacetamide; ethers such as tetrahydrofuran and dioxane; carbon disulfide and liquid sulfur dioxide.

The reaction temperature which can be employed in the reaction between the secalonic acid (II) and the N-methylol derivative (III) or the biscarbamate (IV) is typically from −30° C. to 100° C. and preferably from 0° C. to 80° C. The reaction period of time which can be employed in the reaction is typically from 0.5 to 48 hours, and preferably one to 24 hours.

The amount of the N-methylol derivative (III) or the biscarbamate (IV) which can be employed is one to 10 mols, preferably 2 to 4 mols, per mol of the secalonic acid (II).

The reaction product can be separated by the conventional method such as chromatography and recrystallization to isolate the secalonic acid derivative (I) of this invention. For example, the reaction solution is added to a saturated aqueous sodium chloride solution cooled at about −20° C. to about −10° C. or a mixture of ice and water to separate crystals. The crystals thus obtained are washed and purified by recrystallization or chromatography to isolate the pure secalonic acid derivative (I).

Another method for preparing the secalonic acid derivative of the formula (Ia) comprises reacting 4,4′-bis(aminomethyl)-secalonic acid of the formula (V) with a chloroformic acid ester of the formula (VI):

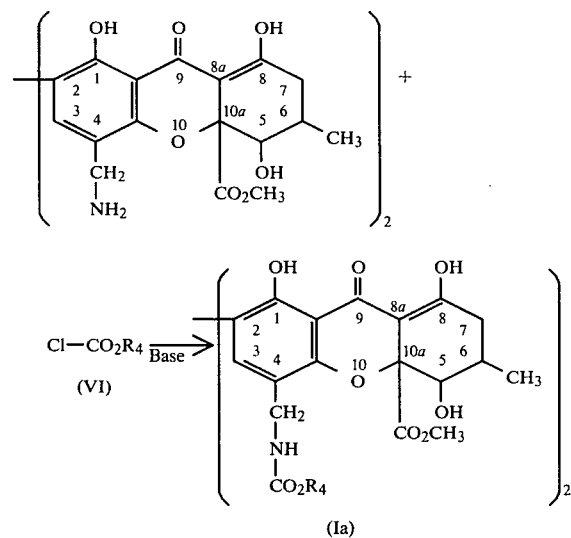

wherein $R_4$ is the same as defined in the formula (I).

This reaction is carried out by dissolving or suspending 4,4′-bis(aminomethyl)-secalonic acid (V) in a solvent and reacting the compound of the formula (V) with the chloroformic acid ester (VI) in the presence of a base.

The solvents which can be employed in the reaction between the 4,4′-bis(aminomethyl)-secalonic acid (V) and the chloroformic acid ester (VI) include alcohols such as methyl alcohol and ethyl alcohol; ethers such as tetrahydrofuran and dioxane; ketones such as acetone and methyl ethyl ketone; carboxylic acids such as acetic acid and propionic acid; nitriles such as acetonitrile; nitrogen-containing compounds such as formamide, N,N-dimethylformamide and N,N-dimethylacetamide; dimethyl sulfoxide and the mixture thereof.

The reaction temperature which can be employed in the reaction between the 4,4′-bis(aminomethyl)-secalonic acid (V) and the chloroformic acid ester (VI) is typically from −30° C. to 100° C., and preferably from 0° C. to 80° C. The reaction period of time which can be usually employed in the reaction is typically from 5 to 180 minutes and preferably 10 to 60 minutes.

The amount of the chloroformic acid ester (VI) which can be employed is 0.5 to 10 mols, preferably one to 5 mols per mol of the 4,4-bis(aminomethyl)-secalonic acid (V).

Exemplary bases which can be employed in the reaction between the 4,4′-bis(aminomethyl)-secalonic acid (V) and the chloroformic acid ester (VI) include inorganic bases such as sodium hydroxide, sodium carbonate and sodium bicarbonate; and organic bases such as triethylamine, tributylamine, N-methylmorpholine and pyridine. The amount of the bases which can be employed is typically one to 10 mols, preferably 2 to 5 mols per mol of the 4,4′-bis(aminomethyl)-secalonic acid (V).

After the completion of the reaction between the 4,4′-bis(aminomethyl)-secalonic acid (V) and the chloroformic acid ester (VI), the reaction solution is added with water to separate crystals. The crystals are treated with conventional methods such as washing, recrystallization and chromatography to isolate the secalonic acid derivatives (I). The secalonic acid derivatives (I) can be converted to the salts thereof by reacting the secalonic acid derivatives (I) with metal hydroxides, metal chlorides, metal sulfates, ammonia or amines. Preferred metal hydroxides, metal chlorides and metal sulfates include sodium hydroxide, potassium hydroxide, magnesium hydroxide, calcium hydroxide, ferric chloride, aluminum chloride, cupric sulfate and ferrous chloride.

The secalonic acid derivatives (I) and the salts thereof of this invention show a lower toxicity compared with the secalonic acid of the formula (II). Moreover, since the secalonic acid derivatives and salts thereof have stronger antitumor activity, they are useful as antitumor agents. Usual excipients can be employed to prepare the antitumor agents. The secalonic acid derivatives of this invention are also useful as intermediates for producing other pharmaceuticals.

The antitumor activity of the secalonic acid derivatives (I) and salts thereof was measured by the following method.

ANTITUMOR ACTIVITY TEST $1 \times 10^6$ cells/mouse of Ehrlich tumor cells were transplanted into abdominal cavities of ICR mice, each group consisting of 7 animals. On the second and the fourth days after the transplant, the mice were abdominally administered with a test compound which was dissolved or suspended in a distilled water containing 0.5% CMC or a physiological salt solution once a day. The ratio (%) of the life of tested animal groups to the life of untreated animal groups was represented as a rate of prolongation life (T/C).

The antitumor activity test result of the secalonic acid derivatives of this invention are shown in Table 1. The abbreviations SA, SB, SC, SD, SE, SF and SG show secalonic acids A, B, C, D, E, F and G, respectively, in this invention.

TABLE 1

| Compound No. | Test Compound | Dose (mg/kg/day) | T/C (%) |
|---|---|---|---|
| | Secalonic Acid A | 32 | 65 (including poisonous death) |
| | | 16 | 115 |
| | | 8 | 135 |
| | Secalonic Acid D | 16 | 51 (including poisonous death) |
| | | 8 | 147 |
| | | 4 | 147 |
| 1 | 4,4'-Bis(maleimidomethyl)-SA | 400 | 173 |
| 2 | 4,4'-Bis(maleimidomethyl)-SD | 400 | 184 |
| 3 | 4,4'-Bis(α-methylmaleimidomethyl)-SB | 200 | 148 |
| 4 | 4,4'-Bis(α,β-dimethylmaleimidomethyl)-SE | 400 | 155 |
| 5 | 4,4'-Bis(phthalimidomethyl)-SD | 400 | 311 |
| | | 200 | 271 |
| 6 | 4,4'-Bis(phthalimidomethyl)-SF | 200 | 280 |
| 7 | 4,4'-Bis(3-methylphthalimidomethyl)-SD | 200 | 305 |
| | | 100 | 275 |
| 8 | 4,4'-Bis(3-chlorophthalimidomethyl)-SD | 400 | 295 |
| 9 | 4,4'-Bis(2-methoxyphthalimidomethyl)-SD | 200 | 268 |
| 10 | 4,4'-Bis(ethoxycarbonylaminomethyl)-SA | 200 | 159 |
| 11 | 4,4'-Bis(ethoxycarbonylaminomethyl)-SD | 128 | 170 |
| 12 | 4,4'-Bis(ethoxycarbonylaminomethyl)-SD-sodium salt | 64 | 185 |
| 13 | 4,4'-Bis(n-butoxycarbonylaminomethyl)-SA-sodium salt | 64 | 163 |
| 14 | 4,4'-Bis(n-butoxycarbonylaminomethyl)-SD | 400 | 232 |
| 15 | 4,4'-Bis(n-butoxycarbonylaminomethyl)-SD-sodium salt | 64 | 220 |
| 16 | 4,4'-Bis(n-docosyloxycarbonylaminomethyl)-SA | 200 | 162 |
| 17 | 4,4'-Bis(2-ethoxyethyloxycarbonylamino-methyl)-SD | 200 | 198 |
| 18 | 4,4'-Bis(phenyloxycarbonylaminomethyl)-SE | 200 | 176 |
| 19 | 4,4'-Bis(phenyloxycarbonylaminomethyl)-SF | 200 | 168 |
| 20 | 4,4'-Bis(n-pentyloxycarbonylaminomethyl)-SD-aluminium salt | 400 | 208 |
| 21 | 4,4'-Bis(n-propyloxycarbonylaminomethyl)-SA | 400 | 211 |

The following examples illustrate the present invention in more detail, but they are given for illustrative purposes only and are not to be construed as limiting the invention.

EXAMPLE 1

In 80 ml of methanesulfonic acid was dissolved 1.3 g (2 mM) of secalonic acid A, and to the solution was added 0.5 g (4 mM) of N-methylolmaleimide at 15° C. The reaction was carried out at 20° C. with stirring for 3 hours. The reaction solution was added to 200 ml of a saturated aqueous sodium chloride solution cooled at about −15° C. to separate crystals. The crystals were obtained by filtration and washed with water and then recrystallized from chloroform-methyl alcohol to give 0.9 g of yellow powdery crystals. The crystals were identified as 4,4'-bis(maleimidomethyl)-secalonic acid A (Compound 1) by the following UV and NMR spectra.

UV Spectrum (CHCl$_3$): λmax: 339 nm

NMR Spectrum (DMSO-d$_6$): δppm: 1.10(d, 6H), 2.2–2.8(m, 6H), 3.64(s, 6H), 3.93(d, 2H), 4.74(s, 4H), 5.25(d, 2H), 7.11(s, 4H), 7.30(s, 2H), 11.7(s, 2H), 12.3–14.0(2H)

The Compound 1 has a strong antitumor activity for Ehrlich ascites carcinoma as shown in Table 2.

TABLE 2

| Antitumor Test for Ehrlich Ascites Carcinoma | |
|---|---|
| Dose (mg/kg/day) | T/C (%) |
| 400 | 173 |
| 200 | 157 |
| 100 | 145 |

EXAMPLE 2

In 200 ml of methanesulfonic acid was dissolved 2.6 g (4 mM) of secalonic acid D, and to the solution was added 1.2 g (9.5 mM) of N-methylolmaleimide at 15° C. The reaction was carried out at 20° C. with stirring for 3 hours. The reaction solution was added to 400 ml of a mixture of ice and water to separate crystals. The crystals were obtained by filtration and washed with water and methyl alcohol. The crystals were recrystallized from chloroform-methyl alcohol to give 2.0 g of yellow powdery crystals. The crystals were identified as 4,4'-bis(maleimidomethyl)-secalonic acid D (Compound 2) by the following UV and NMR spectra. The Compound 2 has strong antitumor activity.

UV Spectrum (CDCl$_3$): λmax: 338 nm

NMR Spectrum (DMSO-d$_6$): δppm: 1.08(d, 6H), 2.2–2.8(m, 6H), 3.63(s, 6H), 3.92(d, 2H), 4.72(s, 4H), 5.24(d, 2H), 7.10(s, 4H), 7.33(s, 2H), 11.6(s, 2H), 12.5–14.5(2H)

EXAMPLES 3–6

The same procedures as described in Example 1 were repeated except that 1.3 g each of secalonic acids B, C, F and G was employed instead of secalonic acid A and reacted with 0.6 g of N-methylol α-methylmaleimide, respectively. The results are shown in Table 3. All the compounds thus obtained have a strong antitumor activity.

TABLE 3

| Example No. | Secalonic Acid | Product | Yield (g) | UV Spectrum λmax (nm) |
| --- | --- | --- | --- | --- |
| 3 | Secalonic Acid B (SB) | 4,4'-Bis(α-methylmaleimidomethyl)-SB (Compound 3) | 0.8 | 339 (CHCl$_3$) |
| 4 | Secalonic Acid C (SC) | 4,4'-Bis(α-methylmaleimidomethyl)-SC | 0.6 | 340 (CHCl$_3$) |
| 5 | Secalonic Acid F (SF) | 4,4'-Bis(α-methylmaleimidomethyl)-SF | 0.7 | 338 (Dioxane) |
| 6 | Secalonic Acid G (SG) | 4,4'-Bis(α-methylmaleimidomethyl)-SG | 0.9 | 338 (Dioxane) |

EXAMPLE 7

In a mixture of 100 ml of dichloromethane and 100 ml of methanesulfonic acid was dissolved 2.6 g (4 mM) of secalonic acid E, and to the solution was added 1.2 g (9.5 mM) of N-methylol-α,β-dimethylmaleimide at 15° C. The reaction was carried out at 20° C. with stirring for 24 hours. After removing the dichloromethane by distillation, the reaction solution was added to 400 ml of a mixture of ice and water to separate crystals. The crystals were obtained by filtration and washed with water and methyl alcohol. The crystals were recrystallized from chloroform-methyl alcohol to give 1.8 g of yellow powder. The powder was identified as 4,4'-bis-(α,β-dimethylmaleimidomethyl)-secalonic acid E (Compound 4). The Compound 4 has strong antitumor activity and the following UV spectrum.

UV Spectrum (Dioxane): λmax: 338 nm

EXAMPLE 8

In 100 ml of methanesulfonic acid was dissolved 1.9 g (3 mM) of secalonic acid D, and to the solution was added 1.1 g of (6 mM) of N-methylolphthalimide at 15° C. The reaction was carried out at 20° C. for 3 hours. The reaction solution was added to 400 ml of a saturated aqueous sodium chloride solution cooled at about −15° C. to separate crystals. The crystals were obtained by filtration and washed with water and methyl alcohol, and then dried to give 2.3 g of yellow crystals. The crystals were recrystallized from chloroform-methyl alcohol to give 1.8 g of yellow powdery crystals. The crystals were identified as 4,4'-bis(phthalimidomethyl)-secalonic acid D (Compound 5) by the following UV and NMR spectra. The Compound 5 has a strong antitumor activity.

UV Spectrum (CHCl$_3$): λmax: 338 nm

NMR Spectrum (CDCl$_3$): δppm: 1.20(d, 6H), 2.2–2.9(m, 6H), 3.32(s, 6H), 3.92(d, 2H), 4.67(d, 2H), 4.88(s, 4H), 7.72(s, 2H), 7.8–7.9(m, 8H), 11.7(s, 2H)

REFERENTIAL EXAMPLE

In 400 ml of anhydrous chloroform was suspended 7.65 g of 4,4'-bis(phthalimidomethyl)-secalonic acid D, and to the suspension was added dropwise 16 g of hydrazine hydrate with stirring under cooling with ice for 10 minutes. After the mixture was added with 160 ml of absolute ethyl alcohol and stirred at 20° C. for 3 hours and then left to stand overnight at 20° C. The solid was separated from the reaction mixture by the filtration and washed twice with 400 ml of ethyl alcohol in each time. The solid thus obtained was suspended in 150 ml of methyl alcohol and to the suspension was added 16 ml of 1 N hydrochloric acid. The mixture was stirred for one hour and then filtrated. The filtrate was concentrated and dried to give 5.1 g of yellow solid.

The yellow solid was identified as 4,4'-bis(aminomethyl)-secalonic acid D hydrochloric acid salt by the following UV and NMR spectra.

UV Spectrum (MeOH): λmax: 339 nm

NMR Spectrum (DMSO-d$_6$): δppm: 1.10(d, 6H), 2.4–2.8(m, 6H), 3.68(s, 6H), 3.96(d, 2H), 4.12(s, 4H), 7.66(s, 2H), 8.36(s, 6H), 11.4–11.9(2H)

EXAMPLE 9

In a mixed solvent of 50 ml of trifluoroacetic acid and 50 ml of dichloramethane were dissolved 3.2 g (5 mM) of secalonic acid D and 3.6 g (20 mM) of N-methylolphthalimide under cooling with ice, and to the solution was added 0.75 g of trifluoromethanesulfonic acid at 5° C. The reaction was carried out at 5° C. for 48 hours. After removing 80 ml of the solvents from the reaction solution by distillation, the reaction solution was added to 500 ml of a saturated aqueous sodium chloride solution cooled at about −15° C. to separate crystals. The crystals were obtained by filtration and washed with water and methanol, and then dried to give 3.3 g of yellow crystals. The crystals were recrystallized from chloroform-methyl alcohol to give 2.7 g of yellow powdary crystals. The UV and NMR spectra of the crystals are identical with those of the Compound 5 obtained in Example 8. The crystals were identified as 4,4'-bis(phthalimidomethyl)-secalonic acid D.

EXAMPLES 10–12

The same procedures as described in Example 8 were repeated except that 1.9 g each of secalonic acids A, F and G was employed instead of the secalonic acid D. The results are shown in Table 4. All the compounds thus obtained have a strong antitumor activity.

TABLE 4

| Example No. | Secalonic Acid | Product | Yield (g) | UV Spectrum λmax (nm) |
| --- | --- | --- | --- | --- |
| 10 | Secalonic Acid A (SA) | 4,4'-Bis(phthalimidomethyl)-SA | 1.5 | 340 (CHCl$_3$) |
| 11 | Secalonic Acid F (SF) | 4,4'-Bis(phthalimidomethyl)-SF (Compound 6) | 1.5 | 338 (CHCl$_3$) |
| 12 | Secalonic Acid G (SG) | 4,4'-Bis(phthalimidomethyl)-SG | 1.8 | 338 (CHCl$_3$) |

EXAMPLES 13–15

The same procedures as described in Example 8 were repeated except that N-methylol derivatives as set forth in Table 5 were employed instead of the N-methylolphthalimide. The results are shown in Table 5. All the compounds thus obtained have a strong antitumor activity.

TABLE 5

| Example No. | N—Methylol Derivatives | (g) | Product | Yield (g) | UV Spectrum $\lambda$max (nm) |
| --- | --- | --- | --- | --- | --- |
| 13 | N—Methylol-3-methylphthalimide | 1.3 | 4,4'-Bis(3-methyl-phthalimidomethyl)-SD (Compound 7) | 1.5 | 340 (Dioxane) |
| 14 | N—Methylol-3-chlorophthalimide | 1.5 | 4,4'-Bis(3-chloro-phthalimidomethyl)-SD (Compound 8) | 1.9 | 339 (Dioxane) |
| 15 | N—Methylol-2-methoxyphthalimide | 1.4 | 4,4'-Bis(3-methoxy-phthalimidomethyl)-SD (Compound 9) | 1.8 | 339 (Dioxane) |

EXAMPLE 16

In 80 ml of methanesulfonic acid was dissolved 1.3 g (2 mM) of secalonic acid A, and to the solution was added 0.5 g (4 mM) of N-methylol urethane at 15° C. The reaction was carried out at 20° C. with stirring for 4 hours. The reaction solution was added to 200 ml of a saturated aqueous sodium chloride solution cooled at about −15° C. to separate crystals. The crystals were obtained by filtration and washed with water and then recrystallized from chloroform-methyl alcohol to give 1.4 g of yellow powdery crystals. The crystals were identified as 4,4'-bis(ethoxycarbonylaminomethyl)-secalonic acid A (Compound 10) by the following UV and NMR spectra.

UV Spectrum (CHCl$_3$): $\lambda$max: 341 nm

NMR Spectrum (DMSO-d$_6$): $\delta$ppm: 1.11(d, 6H), 1.21(t, 6H), 2.3–2.7(m, 6H), 3.69(s, 6H), 4.04(q, 4H), 4.31(d, 4H), 7.45(s, 2H), 11.7(s, 2H)

The Compound 10 has a strong antitumor activity for Ehrlich ascites carcinoma as shown in Table 6.

TABLE 6

| Antitumor Test for Ehrlich Ascites Carcinoma | |
| --- | --- |
| Dose (mg/kg/day) | T/C (%) |
| 400 | 145 |
| 200 | 159 |
| 128 | 155 |
| 64 | 145 |

EXAMPLE 17

In 160 ml of methanesulfonic acid was dissolved 2.55 g (4 mM) of secalonic acid D, and to the solution was added 1.69 g (8 mM) of methylenediurethane at 20° C. The reaction was carried out at 20° C. with stirring for 3 hours. The reaction solution was added to a saturated aqueous sodium chloride solution cooled at a temperature of from −10° C. to −20° C. to separate crystals. The crystals were obtained by filtration and washed with water and then recrystallized from chloroform-methyl alcohol to give 2.78 g of light yellow powdery crystals. The crystals were identified as 4,4'-bis(ethoxycarbonylaminomethyl)-secalonic acid D (Compound 11) by the following UV and NMR spectra. The Compound 11 has a strong antitumor activity.

UV Spectrum (CHCl$_3$): $\lambda$max: 340 nm

NMR Spectrum (DMSO-d$_6$): $\delta$ppm: 1.10(d, 6H), 1.20(t, 6H), 2.4–2.7(m, 6H), 3.68(s, 6H), 4.04(q, 4H), 4.30(d, 4H), 7.46(s, 2H), 11.60(s, 2H)

EXAMPLE 18

In 4 l of methyl alcohol was suspended 8.7 g of 4,4'-bis(ethoxycarbonylaminoethyl)-secalonic acid D produced by the method of Example 17. To the suspension was added dropwise 415 ml of a 0.1 N sodium ethylate methyl alcohol solution at 3°–5° C. under cooling with ice with stirring, and further 3 l of methyl alcohol was added thereto. The solution thus obtained was concentrated four times at 0° C. or below to give 8.3 g of yellow crystals in total. The crystals were identified as 4,4'-bis(ethoxycarbonylaminomethyl)-secalonic acid D sodium salt (Compound 12) by the following UV and NMR spectra. The Compound 12 has a strong antitumor activity.

UV Spectrum (CH$_3$OH): $\lambda$max: 356 nm

NMR Spectrum (DMSO-d$_6$): $\delta$ppm: 1.00(d, 6H), 1.16(t, 6H), 1.9–2.4(m, 6H), 3.52(s, 6H), 4.0–4.4(m, 6H), 5.33(d, 2H), 7.07(s, 2H)

EXAMPLE 19

In 80 ml of methanesulfonic acid was dissolved 1.3 g (2 mM) of secalonic acid A, and to the solution was added 0.6 g (4 mM) of N-methylolcarbamic acid n-butyl ester at 15° C. The reaction was carried out at 20° C. with stirring for 4 hours. The reaction solution was added to 200 ml of a mixture of ice and water to separate crystals. The crystals were obtained by filtration and washed with water and then recrystallized from chloroform to give 1.2 g of yellow powdery crystals. The crystals were identified as 4,4'-bis(n-butoxycarbonylaminomethyl)-secalonic acid A. This compound has a strong antitumor activity and the following UV spectrum.

UV Spectrum (CHCl$_3$): $\lambda$max: 339 nm

EXAMPLE 20

In 90 ml of methyl alcohol was dissolved 1.5 g of 4,4'-bis(aminomethyl)-secalonic acid D hydrochloric acid salt which had been obtained in Referential Example. To the solution was added 3 ml of chloroformic acid n-butyl ester at 5° C. or below under cooling with ice and dropwise 5 ml of triethylene at the same temperature with stirring. The reaction was carried out for 20 minutes and the pH of the reaction solution was adjusted to 3 with a 0.5 N hydrochloric acid. To the reaction solution was added 100 ml of water to separate crystals. The crystals were obtained by filtration and washed with ethyl alcohol and water, and then recrystallized from chloroform to give 1 g of yellow powdery crystals. The crystals were identified as 4,4'-bis(n-butoxycarbonylaminomethyl)-secalonic acid D (Compound 14) by the following UV and NMR spectra. The Compound 14 has a strong antitumor activity.

UV Spectrum (CH₃OH): λmax: 354 nm

NMR Spectrum (DMSO-d₆) δppm: 0.92(t, 6H), 1.11(d, 6H), 1.2–1.8(m, 8H), 2.2–2.8(m, 6H), 3.64(s, 6H), 3.8–4.1(m, 6H), 4.24(d, 4H), 5.87(d, 2H), 7.34(s, 2H), 11.4–12(2H)

EXAMPLE 21

In 100 ml of methyl alcohol was suspended 0.63 g of 4,4'-bis(n-butoxycarbonylaminomethyl)-secalonic acid D which had been obtained in Example 20, and to the suspension was added dropwise 15 ml of 28% sodium ethylate methyl alcohol solution at 3°–5° C. under cooling with ice with stirring. After the insoluble residue was removed by filtration, the filtrate was concentrated twice at 0° C. or below to give 0.59 g of yellow crystals in total. The crystals were identified as 4,4'-bis(n-butoxycarbonylaminomethyl)-secalonic acid D sodium salt (Compound 15) by the following UV and NMR spectra. The Compound 15 has a strong antitumor activity.

UV Spectrum (CH₃OH): λmax: 355 nm

NMR Spectrum (DMSO-d₆): δppm: 0.92(m, 12H), 1.1–1.7(m, 8H), 1.7–2.4(m, 6H), 3.52(s, 6H), 3.6–4.4(m, 6H), 5.30(s, 2H), 7.05(s, 2H)

EXAMPLE 22

In 100 ml of methyl alcohol was suspended 1.0 g of 4,4'-bis(n-butoxycarbonylaminomethyl)-secalonic acid A which had been obtained in Example 19, and to the suspension was added dropwise 15 ml of 28% sodium methylate methyl alcohol solution at 3°–5° C. under cooling with stirring. After the insoluble residue was removed by filtration, the filtrate was concentrated twice at 0° C. or below to give 0.9 g of crystals. The crystals were identified as 4,4'-bis(n-butoxycarbonylaminomethyl)-secalonic acid A sodium salt (Compound 13). The Compound 13 has a strong antitumor activity and the following UV spectrum.

UV Spectrum (CH₃OH): λmax: 355 nm

EXAMPLE 23–41

In 90 ml each of methyl alcohol was added 1.5 g of 4,4'-bis(aminomethyl)-secalonic acid D hydrochloric acid salt, and to the solutions were added 15 mM of chloroformic acid esters as set forth in Table 7 at 5° C. or below under cooling with ice, respectively. To the each solution was added dropwise 5 ml of triethylamine at 5° C. or below with stirring and the reaction was carried out for 20 minutes. The pH of the reaction solution was adjusted to 3 with 0.5 N hydrochloric acid and the reaction solution was added with 100 ml of water to separate crystals. The crystals were obtained by filtration and washed with ethyl alcohol and water, and then recrystallized from chloroform to give the compounds as set forth in Table 7. All the compounds thus obtained have a strong antitumor activity.

TABLE 7

| Example No. | Chloroformic Acid Ester | Product | Yield (g) | UV Spectrum (CHCl₃) λmax (nm) |
|---|---|---|---|---|
| 23 | Chloroformic Acid Methyl Ester | 4,4'-Bis(methoxycarbonylaminomethyl)-SD | 0.6 | 339 |
| 24 | Chloroformic Acid Ethyl Ester | 4,4'-Bis(ethoxycarbonylaminomethyl)-SD | 0.8 | 340 |
| 25 | Chloroformic Acid n-Propyl Ester | 4,4'-Bis(n-propyloxycarbonylaminomethyl)-SD | 0.9 | 340 |
| 26 | Chloroformic Acid iso-Butyl Ester | 4,4'-Bis(iso-butyloxycarbonylaminomethyl)-SD | 0.9 | 339 |
| 27 | Chloroformic Acid n-Pentyl Ester | 4,4'-Bis(n-pentyloxycarbonylaminomethyl)-SD | 0.9 | 339 |
| 28 | Chloroformic Acid n-Hexyl Ester | 4,4'-Bis(n-hexyloxycarbonylaminomethyl)-SD | 1.1 | 340 |
| 29 | Chloroformic Acid n-Nonyl Ester | 4,4'-Bis(n-nonyloxycarbonylaminomethyl)-SD | 1.3 | 340 |
| 30 | Chloroformic Acid 2,2,2-Trichloroethyl Ester | 4,4'-Bis(2,2,2-trichloroethyloxycarbonylaminomethyl)-SD | 1.1 | 337 |
| 31 | Chloroformic Acid Vinyl Ester | 4,4'-Bis(vinyloxycarbonylaminomethyl)-SD | 0.4 | 340 |
| 32 | Chloroformic Acid Allyl Ester | 4,4'-Bis(allyloxycarbonylaminomethyl)-SD | 1.0 | 340 |
| 33 | Chloroformic Acid 2-Ethoxyethyl Ester | 4,4'-Bis(2-ethoxyethyloxycarbonylaminomethyl)-SD (Compound 17) | 1.1 | 339 |
| 34 | Chloroformic Acid iso-Propyl Ester | 4,4'-Bis(iso-propyloxycarbonylaminomethyl)-SD | 0.9 | 339 |
| 35 | Chloroformic Acid t-Butyl Ester | 4,4'-Bis(t-butyloxycarbonylaminomethyl)-SD | 0.5 | 339 |
| 36 | Chlorofomric Acid Cyclohexyl Ester | 4,4'-Bis(cyclohexyloxycarbonylaminomethyl)-SD | 1.0 | 340 |
| 37 | Chloroformic Acid Phenyl Ester | 4,4'-Bis(phenyloxycarbonylaminomethyl)-SD | 1.1 | 339 |
| 38 | Chloroformic Acid p-Nitrophenyl Ester | 4,4'-Bis(p-nitrophenyloxycarbonylaminomethyl)-SD | 1.2 | 340 |
| 39 | Chloroformic Acid Benzyl Ester | 4,4'-Bis(benzyloxycarbonylaminomethyl)-SD | 0.9 | 341 |
| 40 | Chloroformic Acid 2-Chloroethyl Ester | 4,4'-Bis(2-chloroethyloxycarbonylaminomethyl)-SD | 0.9 | 340 |
| 41 | Chloroformic Acid 2-Nitroethyl Ester | 4,4'-Bis(2-nitroethyloxycarbonylaminomethyl)-SD | 0.8 | 341 |

EXAMPLE 42

In 90 ml of methyl alcohol was dissolved 1.5 g of 4,4'-bis(aminomethyl)-secalonic acid E hydrochloric acid salt, and to the solution was added 3 ml of chloroformic acid phenyl ester at 5° C. or below under cooling with ice. To the solution was added dropwise 3 ml of triethylamine at 5° C. or below with stirring and the reaction was carried out for 30 minutes. The pH of the reaction solution was adjusted to 3 with a 0.5 N hydrochloric acid and to the reaction solution was added 100 ml of water to separate crystals. The crystals were obtained by filtration and washed with ethyl alcohol and water, and then recrystallized from chloroform to give 0.9 g of yellow powdery crystals. The crystals were identified as 4,4'-bis(phenyloxycarbonylaminomethyl)-secalonic acid E (Compound 18). The Compound 18 has a strong antitumor activity and the following UV spectrum.

UV Spectrum (CHCl$_3$): λmax: 340 nm

EXAMPLE 43

In 90 ml of methyl alcohol was dissolved 1.5 g of 4,4'-bis(aminomethyl)-secalonic acid F hydrochloric acid salt, and to the solution was added 3 ml of chloroformic acid phenyl ester at 5° C. or below under cooling with ice. To the solution was further added dropwise 3 ml of triethylamine at 5° C. or below with stirring and the reaction was carried out for 30 minutes. The pH of the reaction solution was adjusted to 3 with 0.5 N hydrochloric acid and to the reaction was added 100 ml of water to separate crystals. The crystals were obtained by filtration and washed with ethyl alcohol and water, and then recrystallized from chloroforom to give 0.95 g of the compound. The compound was identified as 4,4'-bis(phenyloxycarbonylaminomethyl)-secalonic acid F (Compound 19). The Compound 19 has a strong antitumor activity and the following UV spectrum.

UV Spectrum (CHCl$_3$): λmax: 340 nm

EXAMPLES 44 AND 45

In 80 ml each of methanesulfonic acid was dissolved 1.3 g (2 mM) of secalonic acid A, and to the solutions was added 0.6 g (4 mM) of N-methylolcarbamic acid ester as set forth in Table 8 at 15° C. The reactions were carried out at 20° C. with stirring for 4 hours. To each 200 ml of a mixture of ice and water were added the reaction solutions, respectively, to separate crystals. The crystals were obtained by filtration, washed with water and then recrystallized from chloroform to give the compounds as set forth in Table 8. These compounds have a strong antitumor activity, respectively.

TABLE 8

| Example No. | N—Methylolcarbamic Acid Ester | Product | Yield (g) | UV Spectrum (CHCl$_3$) λmax (nm) |
|---|---|---|---|---|
| 44 | N—Methylolcarbamic Acid n-Propyl Ester | 4,4'-Bis(n-propyloxycarbonyl-aminomethyl)-SA (Compound 21) | 1.1 | 339 |
| 45 | N—Methylolcarbamic Acid n-docosyl Ester | 4,4'-Bis(n-docosyloxycarbonyl-aminomethyl)-SA (Compound 16) | 1.4 | 338 |

EXAMPLE 46–49

In 160 ml each of methanesulfonic acid was dissolved 2.55 g (4 mM) of secalonic acid D, and to the solutions were added 8 mM of a methylenebis-alkyl urethane as set forth in Table 9, respectively, and 1 ml of BF$_3$-etherate at 20° C. The reactions were carried out at 20° C. with stirring for 3 hours. The each reaction solution was added to a saturated aqueous sodium chloride solution which was cooled at a temperature of from −10° C. to −20° C. to separate crystals. The crystals were obtained by filtration, washed with water and then recrystallized from chloroform-methyl alcohol to give the compounds as set forth in Table 9. These compounds have a strong antitumor activity, respectively.

TABLE 9

| Example No. | Methylene-Bis-Alkyl Urethane | Product | Yield (g) | UV Spectrum (CHCl$_3$) λmax (nm) |
|---|---|---|---|---|
| 46 | Methylene-Bis-n-Butyl Urethane | 4,4'-Bis(n-butoxycarbonyl-aminomethyl)-SD | 2.9 | 339 |
| 47 | Methylene-Bis-n-Pentyl Urethane | 4,4'-Bis(n-pentyloxycarbonyl-aminomethyl)-SD | 2.9 | 340 |
| 48 | Methylene-Bis-iso-Pentyl Urethane | 4,4'-Bis(iso-pentyloxycarbonyl-aminomethyl)-SD | 2.7 | 339 |
| 49 | Methylene-Bis-n-Hexyl Urethane | 4,4'-Bis(n-hexyloxycarbonyl-aminomethyl)-SD | 3.1 | 340 |

EXAMPLE 50

In 100 ml of chloroform was dissolved 1 g of 4,4'-bis(n-pentyloxycarbonylaminomethyl)-SD which had been obtained in Example 27. To the solution was added 14 ml of AlCl$_3$ ethyl alcohol solution (0.2 mol/l) and the solution was stirred for one hour. After removing the solvent from the solution under reduced pressure, the solution was dried to give 1.1 g of yellowish orange solid. The solid was identified as 4,4'-bis(n-pentyloxycarbonylaminomethyl)-secalonic acid D aluminum salt (Compound 20). The Compound 20 has a strong antitumor activity and the following UV spectrum.

UV Spectrum (C$_2$H$_5$OH): λmax: 362 nm

What is claimed is:

1. A secalonic acid having the formula (I):

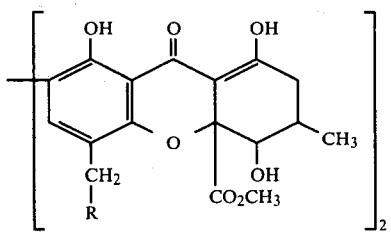
(I)

wherein R is

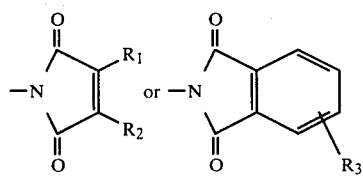

wherein $R_1$ and $R_2$ each independently is a hydrogen atom or a $C_{1-4}$ alkyl group; $R_3$ is a hydrogen atom, a $C_{1-4}$ alkyl group, a $C_{1-5}$ alkoxy group or a halogen atom;

and the pharmaceutically acceptable salts thereof.

2. The compound of claim 1, wherein $R_1$ and $R_2$ each independently is a hydrogen atom or a methyl group.

3. The compound of claim 1, wherein $R_3$ is a hydrogen atom, a methyl group, a methoxy group or a chlorine atom.

4. The compound of claim 1, wherein R is

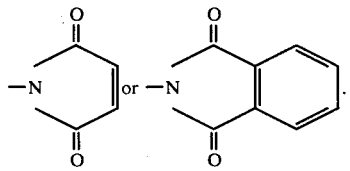

5. The compound of claim 1, wherein the secalonic acid is secalonic acid A, D, E, F or G.

6. The compound of claim 1, wherein the pharmaceutically acceptable salt is the salt of sodium, potassium, or aluminum.

7. An antitumor composition which comprises an effective amount of the secalonic acid compound or its salts of claim 1 as an active ingredient and a pharmaceutically acceptable excipient.

* * * * *